United States Patent [19]

Daute et al.

[11] Patent Number: 5,380,886
[45] Date of Patent: Jan. 10, 1995

[54] PROCESS FOR THE PRODUCTION OF EPOXIDE RING OPENING PRODUCTS HAVING A DEFINED RESIDUAL EPOXIDE OXYGEN CONTENT

[75] Inventors: Peter Daute, Essen; Roland Gruetzmacher, Wuelfrath; Nicole Mertscheit, Hilden, all of Germany

[73] Assignee: Henkel Kommanditgesellschaft Auf Aktien, Duesseldorf, Germany

[21] Appl. No.: 140,184

[22] PCT Filed: Apr. 29, 1992

[86] PCT No.: PCT/EP92/00932

§ 371 Date: Nov. 4, 1993

§ 102(e) Date: Nov. 4, 1993

[87] PCT Pub. No.: WO92/19577

PCT Pub. Date: Nov. 12, 1992

[30] Foreign Application Priority Data

May 8, 1991 [DE] Germany ............... 4115146

[51] Int. Cl.⁶ ............... C07D 301/00; C07D 303/12; C07D 303/42
[52] U.S. Cl. ............... 549/539; 549/513; 549/562
[58] Field of Search ............... 549/539, 562, 513

[56] References Cited

U.S. PATENT DOCUMENTS

| | | | |
|---|---|---|---|
| 2,372,615 | 3/1945 | Thomas et al. | 260/611 |
| 2,485,160 | 10/1949 | Niederhauser et al. | 260/348 |
| 3,453,251 | 7/1969 | Royals et al. | 549/539 |
| 4,057,589 | 11/1977 | Bacskai | 260/635 |
| 4,886,893 | 12/1989 | Meffert et al. | 549/562 |

FOREIGN PATENT DOCUMENTS

| | | |
|---|---|---|
| 0127810 | 5/1984 | European Pat. Off. . |
| 0111626 | 6/1984 | European Pat. Off. . |
| 0257243 | 7/1987 | European Pat. Off. . |
| 0257332 | 3/1988 | European Pat. Off. . |
| 0340587 | 11/1989 | European Pat. Off. . |
| 0361080 | 4/1990 | European Pat. Off. . |
| 0857364 | 11/1952 | Germany . |
| 1261844 | 6/1967 | Germany . |
| 3246612 | 6/1984 | Germany . |

*Primary Examiner*—Joseph E. Evans
*Attorney, Agent, or Firm*—Ernest G. Szoke; Wayne C. Jaeschke; John Daniel Wood

[57] ABSTRACT

A process for the production of epoxide ring opening products having a defined residual epoxide oxygen content by reaction of epoxides with nucleophiles in the presence of medium-strength acids is provided. The products have a defined residual epoxide oxygen content of 10 to 80% by weight based on the epoxide. In the process, aliphatic epoxidized olefins or aliphatic epoxidized esters are reacted with nucleophiles in the presence of 1 to 4 g phosphoric acid, phosphorous acid, or hypophosphorous acid per mol epoxide and the ring opening product is directly obtained without neutralization of the catalyst acid.

21 Claims, No Drawings

PROCESS FOR THE PRODUCTION OF EPOXIDE RING OPENING PRODUCTS HAVING A DEFINED RESIDUAL EPOXIDE OXYGEN CONTENT

BACKGROUND OF THE INVENTION

1. Field of the Invention

This invention relates to epoxide ring opening products having a defined residual epoxide oxygen content and to a process for their production by reaction of epoxides with nucleophiles in the presence of medium-strength acids.

2. Discussion of Related Art

Long-chain polyol compounds containing two or more free hydroxyl groups and a percentage of epoxide groups are valuable raw materials for the production of polymers, for example polyesters, alkyd resins or polyurethane foams.

They are preferably produced from olefins or unsaturated fatty compounds which are epoxidized in a first step. In a second step, the epoxides formed are subjected to ring opening with nucleophiles, for example water or alcohols, resulting in the formation of substances bearing vicinally arranged substituents of which one is a hydroxyl group. This opening of the oxirane ring is the subject of a number of publications.

For example, U.S. Pat. No. 4,057,589 describes a process for the production of tetrols by reaction of unsaturated diols with peracetic acid and subsequent hydrolysis of the epoxides formed at temperatures of at least 120° C.

EP 0 127 810 A1 describes the sulfuric-acid-catalyzed ring opening of epoxides of unsaturated fatty acid esters with alcohols and their subsequent saponification.

DE 3 246 612 A1 describes a process for the production of modified triglycerides in which epoxidized fats or oils are reacted with monohydric or polyhydric alcohols in the presence of sulfuric acid, phosphoric acid or sulfonic acids. The reaction is terminated after a conversion of 20 to 80 mol-%, based on the epoxide groups, by destruction and/or removal of the catalyst and/or the alcohol component.

The catalyst-free pressure hydrolysis of short-chain epoxides containing 3 to 8 carbon atoms and fatty epoxides containing 16 to 22 carbon atoms with water is the subject of EP 0 257 243 A2, EP 0 340 587 A2 and EP 0 361 080 A1.

Finally, EP 0 257 332 B1 describes a process for the continuous production of 1,2-diols in which epoxides are subjected to pressure hydrolysis with water in the presence of acidic catalysts.

However, the production of polyol compounds having a residual epoxide oxygen content by known processes is attended by a number of disadvantages:

Thus, where pressure hydrolysis technology is applied, unwanted secondary products are likely to be formed, for example by transesterification reactions. In addition, the ring opening of the epoxides by this process can only be carried out with water if the necessary outlay on equipment is not to exceed the profitability of the process. Accordingly, only a limited number of products can be obtained by pressure hydrolysis.

If, by contrast, the ring opening of the epoxide compounds is carried out in the presence of acidic catalysts, the residual epoxide oxygen content has to be adjusted by removal or neutralization of the catalyst at a certain epoxide value or by removal of one of the reaction components, for example the nucleophile. This involves increased outlay on equipment.

Accordingly, the problem addressed by the present invention was to provide an improved process for the production of epoxide ring opening products having a defined residual epoxide oxygen content which would be free from the disadvantages mentioned above.

DESCRIPTION OF THE INVENTION

The present invention relates to a process for the production of epoxide ring opening products having a defined residual epoxide oxygen content which is characterized in that epoxide compounds are reacted with nucleophiles in the presence of medium-strength acids from the group consisting of phosphoric acid, phosphorous acid and hypophosphorous acid and the nucleophiles present in excess are then optionally removed without neutralization of the catalyst acid.

It has surprisingly been found that, where the acids mentioned above are used as catalysts in the ring opening of epoxide compounds, the residual epoxide oxygen content is dependent solely upon the quantity of catalyst. The desired epoxide content of the product can therefore be established through the quantity of catalyst before the reaction is actually carried out. This eliminates the need for the neutralization of the catalyst hitherto regarded as essential and for the removal of the nucleophile to adjust the residual epoxide oxygen content.

Epoxide compounds are known substances and may be obtained in known manner by epoxidation of unsaturated starting materials. Examples of corresponding processes are the reaction of olefins with peracetic acid in the presence of acidic catalysts [DE 857 364] or with performic acid formed in situ from formic acid and hydrogen peroxide [U.S. Pat. No. 2,485,160]. For the process according to the invention to be successfully carried out, a substantial percentage, for example 2 to 10% by weight and preferably 4 to 8.5% by weight epoxide oxygen, must be present in the epoxide compounds. This means that not only completely oxidized, but also partly oxidized substances may be used in the process according to the invention.

The epoxide compounds are defined in the following:

a1) Epoxides of olefins corresponding to formula (I):

$$R^1-CH=CH-R^2 \qquad (I)$$

in which $R^1$ is a linear or branched aliphatic hydrocarbon radical containing 1 to 18 carbon atoms and $R^2$ is hydrogen or a linear or branched hydrocarbon radical containing 1 to 8 carbon atoms. Typical examples are the epoxides of oct-1-ene, dec-1-ene, dodec-1-ene, tetradec-1-ene, octadec-1-ene or octadec-9-ene. Epoxides of olefins corresponding to formula (I), in which the sum total of $R^1$ and $R^2$ is a number of 8 to 16, are preferred.

a2) Epoxides of esters corresponding to formula (II):

$$R^3CO-OR^4 \qquad (II)$$

in which $R_3CO$ is an aliphatic acyl radical containing 16 to 24 carbon atoms and 1 to 5 double bonds and $R^4$ is a linear or branched alkyl radical containing 1 to 4 carbon atoms. Typical examples are the epoxides of palmitoleic acid methyl ester, oleic acid methyl ester, elaidic acid methyl ester, petroselic acid methyl ester, linoleic acid methyl ester or erucic acid methyl ester. Epoxides of esters (II), in which $R^3CO$ is an aliphatic hydrocarbon radical containing 18 to 22 carbon atoms and 1 or 2 double bonds and $R^4$ is a methyl group, are preferred.

a3) Epoxides of esters corresponding to formula (III):

$$R^5CO\text{—}OR^6 \qquad (III)$$

in which $R^5CO$ is an aliphatic acyl radical containing 1 to 24 carbon atoms and 0 or 1 to 5 double bonds and $R^6$ is a linear or branched aliphatic hydrocarbon radical containing 16 to 24 carbon atoms and 1 to 5 double bonds. Typical examples are epoxides of acetic acid oleyl ester, oleic acid oleyl ester or erucic acid oleyl ester. Epoxides of esters (III), in which $R^5CO$ is an aliphatic acyl radical containing 18 to 22 carbon atoms and 1 or 2 double bonds and $R^6$ is an aliphatic hydrocarbon radical containing 16 to 22 carbon atoms and 1 or 2 double bonds, are preferred.

a4) Epoxides of glycerol fatty acid esters corresponding to formula (IV):

$$\begin{array}{l}CH_2O\text{—}CO\text{—}R^7 \\ | \\ CH\text{—}O\text{—}CO\text{—}R^8 \\ | \\ CH_2O\text{—}CO\text{—}R^9\end{array} \qquad (IV)$$

in which $R^7CO$ is a linear or branched aliphatic acyl radical containing 16 to 24 carbon atoms and 1 to 5 double bonds and $R^8CO$ and $R^9CO$ independently of one another represent a linear or branched aliphatic acyl radical containing 6 to 22 carbon atoms and 0 or 1 to 5 double bonds and mixtures thereof. Typical examples are epoxides of peanut oil, coriander oil, cottonseed oil, olive oil, linseed oil, beef tallow, fish oil or, more particularly soybean oil. Epoxides of glycerol fatty acid esters (IV), in which $R^7CO$, $R^8CO$ and $R^9CO$ independently of one another represent aliphatic acyl radicals containing 18 to 22 carbon atoms and predominantly 1 or 2 double bonds, are preferably used.

The nucleophiles required for the ring opening of the epoxide compounds may be selected from the following compounds:

b1) Water b2) Alcohols corresponding to formula (V):

$$R^{10}OH \qquad (V)$$

in which $R^{10}$ represents linear or branched aliphatic hydrocarbon radicals containing 1 to 22 carbon atoms and 0 or 1 to 3 double bonds. Typical examples are methanol, ethanol, 1-propanol, 2-propanol, n-butanol, pentanol, hexanol, octanol, decanol, lauryl alcohol, myristyl alcohol, cetyl alcohol, stearyl alcohol, oleyl alcohol, behenyl alcohol or erucyl alcohol. Methanol and ethanol are preferably used.

b3) Polyhydric alcohols selected from the group consisting of ethylene glycol, diethylene glycol, polyethylene glycols having a molecular weight in the range from 300 to 1500, propane-1,2-diol, propane-1,3-diol, glycerol, trimethylol propane, pentaerythritol, sorbitol and sorbitan.

b4) Fatty alcohol polyglycol ethers corresponding to formula (VI):

$$R^{11}O\text{—}(CH_2CHO)_nH \atop {\quad | \atop R^{12}} \qquad (VI)$$

in which $R^{11}$ represents linear or branched aliphatic hydrocarbon radicals containing 6 to 22 carbon atoms and 0 or 1 to 3 double bonds, $R^{12}$ is hydrogen or a methyl group and n is a number of 1 to 30. Typical examples are adducts of on average 1 to 30 mol ethylene and/or propylene oxide with 1 mol hexanol, octanol, decanol, lauryl alcohol, myristyl alcohol, cetyl alcohol, stearyl alcohol, oleyl alcohol, behenyl alcohol or erucyl alcohol. Fatty alcohol polyglycol ethers (VI), in which $R^{11}$ represents $C_{6-18}$ alkyl radicals, $R^{12}$ is hydrogen and n is a number of 1 to 10, are preferably used.

The epoxide compounds and the nucleophiles may be used in molar ratios of 1:5 to 5:1 and preferably in molar ratios of 1:2 to 2:1. The quantity in which the medium-strength acids are used is determined by the residual epoxide oxygen content established in advance. Normally, they may be used in a quantity of 0.1 to 10 g and are preferably used in a quantity of 1 to 4 g per mol epoxide compound which results in the formation of compounds which may have a residual epoxide oxygen content of 10 to 80% by weight, preferably 15 to 55% by weight and more preferably 20 to 35% by weight, based on the epoxide compound used. Phosphorous acid and hypophosphorous acid are preferably used for the process according to the invention.

The partial ring opening may be carried out by methods known per se. It has proved to be of advantage to carry out the reaction at the boiling temperature of the nucleophile used or at a temperature in the range from 100° to 250° C. As mentioned above, there is no need to remove excess nucleophile in order to establish a particular residual epoxide oxygen content. However, this may be advisable for other reasons, for example if there is a risk of the performance properties of the products being affected or if a residual content of the nucleophile is troublesome during subsequent process. In this case, the ring opening may be followed, for example, by distillation.

The products obtainable by the process according to the invention are suitable as starting materials for the production of polymers. For example, they may be incorporated in alkyd resins by condensation both via the epoxide groups and via the hydroxyl functions and represent polyfunctional polycondensation units which are also of importance for the development of polyurethane foams.

Accordingly, the present invention also relates to epoxide ring opening products having a defined residual epoxide oxygen content which are obtainable by reaction of epoxide compounds with nucleophiles in the presence of medium strength acids from the group consisting of phosphoric acid, phosphorous acid and hypophosphorous acid, optionally followed by removal of the nucleophiles present in excess without neutralization.

The following Examples are intended to illustrate the invention without limiting it in any way.

EXAMPLES

Example 1

Ring opening of soybean oil epoxide with methanol. 128 g (4 mol) methanol and 4.7 g 85% by weight phosphoric acid, corresponding to 2 g per mol epoxide, were added to 479 g soybean oil epoxide having an epoxide oxygen content of 6.68% by weight, corresponding to 2 mol epoxide. The mixture was heated with stirring for 3 h to the reflux temperature and then divided into two batches. Batch 1 was neutralized by addition of 1.7 g diethanolamine; batch 2 was not neutralized. Both batches were then freed from unreacted methanol under reduced pressure at approx. 65° C.

Residual epoxide oxygen content batch 1: 4.59% by weight

Residual epoxide oxygen content batch 2: 4.51% by weight

Examples 2 to 5, Comparison Examples C1 and C2

As in Example 1, 128 g (4 mol) methanol and quantities of 1 or 1.2 g of catalyst acids A) to E) per mol epoxide were added to 479 g soybean oil epoxide having an epoxide oxygen content of 6.68% by weight, corresponding to 2 mol epoxide. The mixture was heated with stirring for 6 h to the reflux temperature and the residual epoxide oxygen content was determined as a function of time by regular sampling.

Catalyst acids used
A) Phosphoric acid (85% by weight)
B) Phosphorous acid (100% by weight)
C) Hypophosphorous acid (50% by weight)
D) Sulfuric acid (100% by weight)
E) Sulfosuccinic acid (70% by weight)

Catalyst acids A) to C) correspond to the invention while acids D) and E) are intended for comparison. The results are set out in Table 1.

TABLE 1

Ring opening of soybean oil epoxide with methanol

| Ex. | Catalyst acid | Quantity* g/mol | \multicolumn{7}{c}{Residual epoxide oxygen content (%)#} |
|---|---|---|---|---|---|---|---|---|---|
| | | | 0.5 | 1 | 2 | 3 | 4 | 5 | 6 |
| 2 | A | 1.0 | 4.9 | 4.6 | 4.6 | 4.6 | 4.6 | 4.6 | 4.6 |
| 3 | A | 1.2 | 5.0 | 4.6 | 4.4 | 4.4 | 4.4 | 4.4 | 4.4 |
| 4 | B | 1.0 | 4.6 | 4.3 | 4.0 | 3.9 | 3.8 | 3.8 | 3.8 |
| 5 | C | 1.0 | | 2.5 | 1.6 | 1.3 | 1.0 | 0.8 | 0.7 |
| C1 | D | 1.0 | 4.3 | 4.1 | 3.7 | 3.6 | 3.4 | 2.9 | 2.8 |
| C2 | E | 1.0 | 4.3 | 4.0 | 3.5 | 2.8 | 2.5 | 2.0 | 1.6 |

*Quantity of catalyst in g per mol epoxide
Residual epoxide oxygen content in % by weight after h

We claim:

1. A process for the production of epoxide ring opening products comprising reacting an epoxide compound, said epoxide compound being selected from the group consisting of aliphatic epoxidized olefins or aliphatic epoxidized esters, with a nucleophile in the presence of an acid, said acid being selected from the group consisting of phosphoric acid and phosphorous acid, in an amount of 10 to 4 g of said acid per mol epoxide, wherein the amount of said acid is effective without neutralization of said acid to produce a product having a residual epoxide oxygen content of 10 to 80% by weight based on the epoxide compound.

2. A process as claimed in claim 1 wherein said epoxide compound is an epoxide of an olefin corresponding to formula (I):

$$R^1-CH=CH-R^2 \quad (I)$$

in which $R^1$ is a linear or branched aliphatic hydrocarbon radical containing 1 to 18 carbon atoms and $R^2$ is hydrogen or a linear or branched hydrocarbon radical containing 1 to 8 carbon atoms.

3. A process as claimed in claim 1 wherein said epoxide compound is an epoxide of an ester corresponding to formula (II):

$$R^3CO-OR^4 \quad (II)$$

in which $R^3CO$ is an aliphatic acyl radical containing 16 to 24 carbon atoms and 1 to 5 double bonds and $R^4$ is a linear or branched alkyl radical containing 1 to 4 carbon atoms.

4. A process as claimed claim 1 wherein said epoxide compound is an epoxide of an ester corresponding to formula (III):

$$R^5CO-OR^6 \quad (III)$$

in which $R^5CO$ is an aliphatic acyl radical containing 1 to 24 carbon atoms and 0 or 1 to 5 double bonds and $R^6$ is a linear or branched aliphatic hydrocarbon radical containing 16 to 24 carbon atoms and 1 to 5 double bonds.

5. A process as claimed in claim 1 wherein said epoxide compound is an epoxide of a glycerol fatty acid ester corresponding to formula (IV):

$$\begin{array}{l} CH_2O-CO-R^7 \\ | \\ CH-O-CO-R^8 \\ | \\ CH_2O-CO-R^9 \end{array} \quad (IV)$$

in which $R^7CO$ is a linear or branched aliphatic acyl radical containing 16 to 24 carbon atoms and 1 to 5 double bonds and $R^8CO$ and $R^9CO$ independently of one another represent a linear or branched aliphatic acyl radical containing 6 to 24 carbon atoms and 0 or 1 to 5 double bonds and mixtures thereof.

6. A process as claimed in claim 1 wherein said nucleophile is water.

7. A process as claimed in claim 1 wherein said nucleophile is an alcohol corresponding to formula (V):

$$R^{10}OH \quad (V)$$

in which $R^{10}$ represents linear or branched aliphatic hydrocarbon radicals containing 1 to 22 carbon atoms and 0 or 1 to 3 double bonds.

8. A process as claimed in claim 1 wherein said nucleophile is an alcohol selected from the group consisting of ethylene glycol, diethylene glycol, polyethylene glycols having a molecular weight in the range from 300 to 1500, propane-1,2-diol, propane-1,3-diol, glycerol, trimethylol propane, pentaerythritol, sorbitol and sorbitan.

9. A process as claimed in claim 1 wherein said nucleophile is a fatty alcohol polyglycol ether corresponding to formula (VI):

$$\begin{array}{c} R^{12} \\ | \\ R^{11}O-(CH_2CHO)_nH \end{array} \quad (VI)$$

in which $R^{11}$ represents linear or branched aliphatic hydrocarbon radicals containing 6 to 22 carbon atoms and 0 or 1 to 3 double bonds, $R^{12}$ is hydrogen of a methyl group and n is a number of 1 to 30.

10. A process as claimed in claim 1 wherein said epoxide compound is reacted with said nucleophile in a molar ratio of 1:5 to 5:1.

11. A process as claimed in claim 1 wherein said epoxide compound is reacted with said nucleophile in a molar ratio of 1:2 to 2:1.

12. A process as claimed in claim 1 wherein said reaction is carried out at the boiling temperature of said nucleophile.

13. A process as claimed in claim 1 wherein said reaction is carried out at a temperature in the range from 100° to 250° C.

14. A process as claimed in claim 1 wherein said residual epoxide oxygen content is 15 to 55% by weight based on the epoxide.

15. A process as claimed in claim 1 wherein said residual epoxide oxygen content is 20 to 35% by weight based on the epoxide.

16. A process as claimed in claim 1 further comprising, after said reacting, removing excess nucleophile.

17. A process as claimed in claim 1 wherein further comprising, after said reacting, distilling excess nucleophile.

18. A process of claim 1 wherein said nucleophile is selected from the group consisting of water, a monohydric alcohol, a polyhydric alcohol, and a fatty alcohol polyglycol ether.

19. A process for the production of epoxide ring opening products consisting essentially of reacting an epoxide compound, said epoxide compound being selected from the group consisting of aliphatic epoxidized olefins or aliphatic epoxidized esters, with a nucleophile, said nucleophile being selected from the group consisting of water, a monohydric alcohol, a polyhydric alcohol, and a fatty alcohol polyglycol ether, in the presence of an acid, said acid being selected from the group consisting of phosphoric acid and phosphorous acid, in an amount of 1 to 4 g of said acid per mol epoxide, wherein the amount of said acid is effective, without neutralization of said acid, to produce a product having a residual epoxide oxygen content of 20 to 35% by weight based on said epoxide compound.

20. A composition of matter comprising the product of the process of claim 19.

21. A composition of matter comprising the product of the process of claim 1.

* * * * *